(12) United States Patent
Ivri

(10) Patent No.: US 11,938,057 B2
(45) Date of Patent: *Mar. 26, 2024

(54) HYDRODYNAMICALLY ACTUATED PRESERVATIVE FREE DISPENSING SYSTEM

(71) Applicant: Bausch + Lomb Ireland Limited, Dublin (IE)

(72) Inventor: Yehuda Ivri, Newport Coast, CA (US)

(73) Assignee: Bausch + Lomb Ireland Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 17/509,383

(22) Filed: Oct. 25, 2021

(65) Prior Publication Data
US 2022/0039998 A1 Feb. 10, 2022

Related U.S. Application Data

(63) Continuation-in-part of application No. 17/233,105, filed on Apr. 16, 2021.
(Continued)

(51) Int. Cl.
*A61F 9/00* (2006.01)
*A61B 17/00* (2006.01)

(52) U.S. Cl.
CPC .. *A61F 9/0008* (2013.01); *A61B 2017/00057* (2013.01); *A61B 2017/00889* (2013.01)

(58) Field of Classification Search
CPC ........ G01C 22/02; G04B 47/06; G11B 27/13; A61F 9/0008; A61F 9/0026; A61M 11/00;
(Continued)

(56) References Cited

U.S. PATENT DOCUMENTS 3,640,274 A * 2/1972 Costello ................. A61H 35/02
128/200.14
3,779,245 A 12/1973 Windsor
(Continued)

FOREIGN PATENT DOCUMENTS

CN 103118642 A 5/2013
CN 104146816 A 11/2014
(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.
(Continued)

*Primary Examiner* — Leslie Lopez
*Assistant Examiner* — Seth Han
(74) *Attorney, Agent, or Firm* — Greenberg Traurig, LLP; Chinh Pham; Andrew Cull

(57) ABSTRACT

Multi-dose preservative-free ocular fluid delivery devices are provided. The fluid delivery device includes a fluid dispensing system and a fluid package for storing a liquid therein and supplying said liquid to the dispensing system. The dispensing system comprises an elongated chamber which includes a check valve which defines a frontal closure to the chamber. The valve is normally closed and hermetically seals the chamber. The dispenser includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed.

18 Claims, 7 Drawing Sheets

Related U.S. Application Data

(60) Provisional application No. 63/011,808, filed on Apr. 17, 2020.

(58) Field of Classification Search
CPC ............. A61M 11/001; A61M 11/005; A61M 2210/0612; B05B 17/0646; B05B 17/0623; B05B 17/0607; B05B 11/007; B05B 11/1052; B05B 12/08; B05B 17/0661; B05B 17/063; B05B 17/04; B05B 17/0638; F04B 43/043; F04B 19/006; F04B 43/046; F04B 53/10; F04B 53/108; F04B 53/1072; F04B 53/1005; F04B 43/04
See application file for complete search history.

(56) References Cited

U.S. PATENT DOCUMENTS

| | | | |
|---|---|---|---|
| 3,812,854 A | 5/1974 | Buckles | |
| 3,861,386 A | 1/1975 | Harris | |
| 3,970,250 A | 7/1976 | Drews | |
| 3,976,072 A | 8/1976 | Walker | |
| 4,159,803 A | 7/1979 | Cameto | |
| 4,300,546 A | 11/1981 | Kruber | |
| 4,334,531 A | 6/1982 | Reichl | |
| 4,338,576 A | 7/1982 | Takahashi | |
| 4,344,744 A * | 8/1982 | Schuster | B05B 11/1001 |
| | | | 222/321.9 |
| 4,352,459 A | 10/1982 | Berger | |
| 4,465,234 A | 8/1984 | Maehara | |
| 4,632,311 A | 12/1986 | Nakane | |
| 4,655,393 A | 4/1987 | Berger | |
| 4,793,339 A * | 12/1988 | Matsumoto | B05B 17/0684 |
| | | | 239/338 |
| 4,850,534 A | 7/1989 | Takahashi | |
| 4,882,150 A | 11/1989 | Kaufman | |
| 4,952,581 A | 8/1990 | Bito | |
| 4,961,345 A | 10/1990 | Tsuruoka | |
| 4,976,259 A | 12/1990 | Higson | |
| 4,981,625 A | 1/1991 | Rhim | |
| 5,025,957 A | 6/1991 | Ranalletta | |
| 5,171,306 A | 12/1992 | Vo | |
| 5,232,363 A | 8/1993 | Meller | |
| 5,368,582 A | 11/1994 | Bertera | |
| 5,370,317 A * | 12/1994 | Weston | B05B 11/007 |
| | | | 239/533.13 |
| 5,487,378 A | 1/1996 | Robertson | |
| 5,549,249 A | 8/1996 | Foster | |
| 5,624,057 A | 4/1997 | Lifshey | |
| 5,627,611 A | 5/1997 | Scheiner | |
| 5,630,793 A | 5/1997 | Rowe | |
| 5,657,926 A | 8/1997 | Toda | |
| 5,692,651 A | 12/1997 | Fuchs | |
| 5,811,443 A | 9/1998 | DeSantis, Jr. | |
| 5,828,394 A * | 10/1998 | Khuri-Yakub | B05B 17/0607 |
| | | | 347/68 |
| 5,938,117 A | 8/1999 | Ivri | |
| 5,958,342 A | 9/1999 | Gamble | |
| 5,960,224 A * | 9/1999 | Sanada | G03D 5/04 |
| | | | 396/575 |
| 6,024,717 A | 2/2000 | Ball | |
| 6,062,212 A | 5/2000 | Davison | |
| 6,065,623 A | 5/2000 | Hierzer | |
| 6,095,376 A | 8/2000 | Hennemann | |
| 6,196,218 B1 * | 3/2001 | Voges | B05B 17/0607 |
| | | | 128/200.14 |
| 6,232,129 B1 | 5/2001 | Wiktor | |
| 6,273,092 B1 | 8/2001 | Nolan | |
| 6,302,101 B1 * | 10/2001 | Py | B05B 11/1066 |
| | | | 128/200.22 |
| 6,467,476 B1 | 10/2002 | Ivri | |
| RE38,077 E | 4/2003 | Cohen | |
| 6,543,442 B2 | 4/2003 | Gonda | |
| 6,629,646 B1 | 10/2003 | Ivri | |
| 6,730,066 B1 | 5/2004 | Bennwik | |
| 6,758,837 B2 | 7/2004 | Peclat | |
| 6,869,275 B2 * | 3/2005 | Dante | F04B 43/046 |
| | | | 417/322 |
| 7,066,398 B2 | 6/2006 | Borland | |
| 7,105,357 B1 | 9/2006 | Kalkum | |
| 7,201,732 B2 | 4/2007 | Anderson | |
| 7,314,938 B2 | 1/2008 | Shen | |
| 7,571,722 B2 | 8/2009 | Wuttke | |
| 7,745,460 B2 | 6/2010 | Shen | |
| 7,790,743 B2 | 9/2010 | Shen | |
| 7,874,467 B2 | 1/2011 | Pardes | |
| 7,883,031 B2 * | 2/2011 | Collins, Jr. | A61M 11/042 |
| | | | 239/338 |
| 7,928,122 B2 | 4/2011 | Shen | |
| 8,012,136 B2 | 9/2011 | Collins, Jr. | |
| 8,048,047 B2 | 11/2011 | Domash | |
| 8,056,766 B2 | 11/2011 | Grevin | |
| 8,128,606 B2 | 3/2012 | Anderson | |
| 8,133,210 B2 | 3/2012 | Al-Abdulla | |
| 8,144,399 B2 | 3/2012 | Steenblik | |
| 8,168,655 B2 | 5/2012 | Gadek | |
| 8,273,307 B2 | 9/2012 | Eickhoff | |
| 8,367,701 B2 | 2/2013 | Burnier | |
| 8,398,001 B2 | 3/2013 | Borland | |
| 8,435,544 B2 | 5/2013 | Mitra | |
| 8,544,462 B2 | 10/2013 | Papania | |
| 8,545,463 B2 | 10/2013 | Collins, Jr. | |
| 8,592,450 B2 | 11/2013 | Gadek | |
| 8,629,111 B2 | 1/2014 | Acheampong | |
| 8,633,162 B2 | 1/2014 | Acheampong | |
| 8,642,556 B2 | 2/2014 | Acheampong | |
| 8,648,048 B2 | 2/2014 | Acheampong | |
| 8,684,980 B2 | 4/2014 | Hunter | |
| 8,685,930 B2 | 4/2014 | Acheampong | |
| 8,722,728 B2 | 5/2014 | Wong | |
| 8,733,935 B2 | 5/2014 | Ballou, Jr. | |
| 8,863,998 B2 | 10/2014 | Painchaud | |
| 8,927,574 B2 | 1/2015 | Burnier | |
| 8,927,921 B1 | 1/2015 | Nelms | |
| 8,936,021 B2 | 1/2015 | Collins, Jr. | |
| 9,039,666 B2 | 5/2015 | Voss | |
| 9,068,566 B2 | 6/2015 | Ivri | |
| 9,085,553 B2 | 7/2015 | Zeller | |
| 9,087,145 B2 | 7/2015 | Ballou, Jr. | |
| 9,186,690 B2 | 11/2015 | Scanlon | |
| 9,216,174 B2 | 12/2015 | Shen | |
| 9,238,532 B2 | 1/2016 | Decock | |
| 9,248,191 B2 | 2/2016 | Acheampong | |
| 9,353,088 B2 | 5/2016 | Burnier | |
| 9,447,077 B2 | 9/2016 | Burnier | |
| 9,597,230 B2 | 3/2017 | Haffner | |
| 9,676,525 B2 | 6/2017 | Greiner-Perth | |
| 9,700,686 B2 | 7/2017 | Gavini | |
| 9,801,757 B2 | 10/2017 | Voss | |
| 9,808,825 B2 | 11/2017 | Aguilar | |
| 9,867,933 B2 | 1/2018 | Pardes | |
| 9,890,141 B2 | 2/2018 | Burnier | |
| 10,073,949 B2 | 9/2018 | Ballou, Jr. | |
| 10,105,720 B2 | 10/2018 | Decock | |
| 10,124,000 B2 | 11/2018 | Shen | |
| 10,154,923 B2 | 12/2018 | Hunter | |
| 10,174,017 B2 | 1/2019 | deLong | |
| 10,314,740 B2 | 6/2019 | Kraft | |
| 10,624,781 B2 | 4/2020 | Ivri | |
| 11,278,448 B2 | 3/2022 | Palanker | |
| 2001/0035184 A1 | 11/2001 | Schuler et al. | |
| 2001/0036424 A1 | 11/2001 | Takahashi | |
| 2001/0036449 A1 | 11/2001 | Garst | |
| 2002/0078947 A1 | 6/2002 | Gumaste | |
| 2002/0124843 A1 | 9/2002 | Skiba | |
| 2002/0158196 A1 | 10/2002 | Berggren | |
| 2002/0161344 A1 | 10/2002 | Peclat | |
| 2002/0185125 A1 * | 12/2002 | Klimowicz | A61M 15/0085 |
| | | | 128/200.14 |
| 2002/0190079 A1 * | 12/2002 | Hamamoto | B65D 1/0215 |
| | | | 222/481.5 |
| 2003/0052573 A1 | 3/2003 | Wischnewskiy | |

(56) References Cited

U.S. PATENT DOCUMENTS

| | | | |
|---|---|---|---|
| 2003/0065294 A1 | 4/2003 | Pickup | |
| 2003/0071071 A1 | 4/2003 | Garcia | |
| 2003/0140921 A1 | 7/2003 | Smith | |
| 2004/0039355 A1 | 2/2004 | Gonzalez | |
| 2004/0050861 A1 | 3/2004 | Lisec | |
| 2004/0138630 A1 | 7/2004 | Al-Abdulla | |
| 2004/0163645 A1 | 8/2004 | Connelly | |
| 2004/0173642 A1 | 9/2004 | Clifford | |
| 2004/0204674 A1 | 10/2004 | Anderson | |
| 2004/0215157 A1 | 10/2004 | Peclat | |
| 2004/0256487 A1 | 12/2004 | Collins | |
| 2004/0263567 A1* | 12/2004 | Hess | B05B 17/0638 347/47 |
| 2005/0001981 A1 | 1/2005 | Anderson | |
| 2005/0006417 A1 | 1/2005 | Nicol | |
| 2005/0107832 A1* | 5/2005 | Bernabei | A61N 1/327 607/3 |
| 2005/0172962 A1 | 8/2005 | Gumaste | |
| 2005/0207917 A1* | 9/2005 | Koerner | A61M 15/0065 417/413.2 |
| 2005/0240162 A1* | 10/2005 | Chen | A61F 9/0008 604/298 |
| 2005/0261641 A1 | 11/2005 | Warchol | |
| 2006/0065677 A1 | 3/2006 | Py | |
| 2006/0069358 A1 | 3/2006 | Gerondale | |
| 2006/0147313 A1 | 7/2006 | Zengerle | |
| 2007/0051362 A1 | 3/2007 | Sullivan | |
| 2007/0088267 A1 | 4/2007 | Shekalim | |
| 2007/0088268 A1 | 4/2007 | Edwards | |
| 2007/0102455 A1 | 5/2007 | Stark | |
| 2007/0119969 A1 | 5/2007 | Collins | |
| 2007/0195151 A1 | 8/2007 | Anderson | |
| 2007/0268340 A1 | 11/2007 | Dacquay | |
| 2007/0295332 A1 | 12/2007 | Ziegler et al. | |
| 2008/0039807 A1 | 2/2008 | Pine | |
| 2008/0202514 A1 | 8/2008 | Kriksunov | |
| 2008/0214940 A1 | 9/2008 | Benaron | |
| 2008/0233053 A1 | 9/2008 | Gross | |
| 2008/0247264 A1 | 10/2008 | Gabl | |
| 2008/0257911 A1* | 10/2008 | Choi | B05B 11/007 222/320 |
| 2009/0060793 A1 | 3/2009 | Eickhoff | |
| 2009/0114742 A1 | 5/2009 | Collins, Jr. | |
| 2009/0134235 A1 | 5/2009 | Ivri | |
| 2009/0182291 A1 | 7/2009 | Eilat | |
| 2009/0192443 A1* | 7/2009 | Collins, Jr. | A61M 15/008 239/338 |
| 2009/0212127 A1 | 8/2009 | Reynolds | |
| 2009/0212133 A1* | 8/2009 | Collins, Jr. | A61M 11/041 239/338 |
| 2009/0223513 A1* | 9/2009 | Papania | A61M 15/0065 128/200.14 |
| 2010/0001090 A1* | 1/2010 | Neergaard | B05B 17/0676 239/4 |
| 2010/0005903 A1 | 1/2010 | Beavis | |
| 2010/0013352 A1 | 1/2010 | Pletner | |
| 2010/0044460 A1 | 2/2010 | Sauzade | |
| 2010/0072301 A1 | 3/2010 | Cater | |
| 2010/0072302 A1 | 3/2010 | Cater | |
| 2010/0076388 A1 | 3/2010 | Cater | |
| 2010/0147899 A1 | 6/2010 | Nardi | |
| 2010/0186738 A1 | 7/2010 | Kobayashi et al. | |
| 2010/0222752 A1 | 9/2010 | Collins, Jr. | |
| 2010/0236545 A1 | 9/2010 | Kern | |
| 2010/0295420 A1 | 11/2010 | Wierach | |
| 2010/0326431 A1* | 12/2010 | Yu | A61M 11/005 128/200.14 |
| 2011/0074247 A1 | 3/2011 | Hohlfeld | |
| 2011/0102735 A1 | 5/2011 | Gupta | |
| 2011/0106025 A1* | 5/2011 | Hall | A61F 9/0008 604/298 |
| 2011/0146670 A1* | 6/2011 | Gallem | A61M 15/0036 128/200.14 |
| 2011/0284579 A1 | 11/2011 | Pardes | |
| 2011/0293452 A1 | 12/2011 | Kim | |
| 2012/0017898 A1 | 1/2012 | Moller | |
| 2012/0062840 A1 | 3/2012 | Ballou, Jr. | |
| 2012/0070467 A1 | 3/2012 | Ballou, Jr. | |
| 2012/0143152 A1* | 6/2012 | Hunter | G16H 40/63 604/290 |
| 2012/0179122 A1 | 7/2012 | Eilat | |
| 2012/0197219 A1 | 8/2012 | Scanlon | |
| 2012/0304929 A1 | 12/2012 | Ivri | |
| 2013/0002095 A1 | 1/2013 | Van der Linden | |
| 2013/0017283 A1 | 1/2013 | Zemel | |
| 2013/0025038 A1 | 1/2013 | Frey | |
| 2013/0053042 A1 | 2/2013 | Tanikawa | |
| 2013/0079733 A1* | 3/2013 | Burt | B05B 17/0607 239/102.1 |
| 2013/0118619 A1 | 5/2013 | Loth | |
| 2013/0140225 A1* | 6/2013 | Decock | B05B 11/0008 422/509 |
| 2013/0150812 A1 | 6/2013 | Hunter | |
| 2013/0152796 A1 | 6/2013 | Pawl | |
| 2013/0153677 A1 | 6/2013 | Leen | |
| 2013/0164436 A1* | 6/2013 | Yagi | C23C 18/1216 118/713 |
| 2013/0172830 A1 | 7/2013 | Hunter | |
| 2013/0206857 A1 | 8/2013 | Ivri | |
| 2013/0299607 A1 | 11/2013 | Wilkerson | |
| 2013/0345672 A1 | 12/2013 | Ferreri | |
| 2014/0088524 A1 | 3/2014 | Marx | |
| 2014/0113946 A1 | 4/2014 | Abad | |
| 2014/0157956 A1 | 6/2014 | Date | |
| 2014/0171490 A1 | 6/2014 | Gross | |
| 2014/0187969 A1 | 7/2014 | Hunter | |
| 2014/0214024 A1 | 7/2014 | Eichler | |
| 2014/0224267 A1 | 8/2014 | Levitz | |
| 2014/0242022 A1 | 8/2014 | Vehige | |
| 2014/0249491 A1 | 9/2014 | Ballou, Jr. | |
| 2014/0257172 A1 | 9/2014 | Yalamanchili | |
| 2014/0274910 A1 | 9/2014 | Cumberlidge | |
| 2014/0276054 A1 | 9/2014 | Hossack | |
| 2014/0285121 A1 | 9/2014 | Balogh | |
| 2014/0323931 A1* | 10/2014 | Avni | A61H 23/0254 601/46 |
| 2014/0336596 A1 | 11/2014 | Wochele | |
| 2014/0336618 A1 | 11/2014 | Wilkerson | |
| 2015/0018781 A1* | 1/2015 | Rinderknect | A61F 9/0026 604/298 |
| 2015/0035180 A1 | 2/2015 | Shen | |
| 2015/0036219 A1 | 2/2015 | Shen | |
| 2015/0040891 A1 | 2/2015 | Avni | |
| 2015/0086397 A1 | 3/2015 | Ma | |
| 2015/0097050 A1 | 4/2015 | Ciervo | |
| 2015/0139973 A1 | 5/2015 | Steinfeld | |
| 2015/0144128 A1 | 5/2015 | Hijlkema | |
| 2015/0209174 A1 | 7/2015 | Abreu | |
| 2015/0209178 A1 | 7/2015 | Blakey | |
| 2015/0238689 A1* | 8/2015 | Shimizu | A61M 5/14276 604/67 |
| 2015/0256730 A1 | 9/2015 | Shen | |
| 2015/0276994 A1 | 10/2015 | Shen | |
| 2015/0308421 A1 | 10/2015 | Vogt | |
| 2015/0328151 A1 | 11/2015 | Ballou, Jr. | |
| 2015/0352297 A1 | 12/2015 | Stedman | |
| 2016/0107180 A1 | 4/2016 | Decock | |
| 2016/0120833 A1 | 5/2016 | Wan | |
| 2016/0129467 A1 | 5/2016 | Ciardella | |
| 2016/0199225 A1 | 7/2016 | Ivri | |
| 2016/0199230 A1* | 7/2016 | Doshi | A61F 13/58 156/219 |
| 2016/0213866 A1 | 7/2016 | Tan | |
| 2016/0263314 A1 | 9/2016 | Pardes | |
| 2016/0296367 A1 | 10/2016 | Ivri | |
| 2016/0354559 A1 | 12/2016 | Gavini | |
| 2017/0028626 A1 | 2/2017 | Delrot | |
| 2017/0136484 A1 | 5/2017 | Wilkerson | |
| 2017/0138357 A1* | 5/2017 | Kondo | F04B 53/10 |
| 2017/0151088 A1 | 6/2017 | Ballou, Jr. | |
| 2017/0156927 A1 | 6/2017 | Richter | |
| 2017/0182510 A1 | 6/2017 | Wilkerson | |

(56) References Cited

U.S. PATENT DOCUMENTS

| | | | |
|---|---|---|---|
| 2017/0187969 A1 | 6/2017 | Kitamori | |
| 2017/0274159 A1 | 9/2017 | Gavini | |
| 2017/0344714 A1 | 11/2017 | Ballou, Jr. | |
| 2018/0085251 A1 | 3/2018 | Hunter | |
| 2018/0108275 A1 | 4/2018 | Newberry | |
| 2018/0116871 A1 | 5/2018 | Hunter | |
| 2018/0207030 A1* | 7/2018 | Ivri | B05B 9/0838 |
| 2018/0229247 A1 | 8/2018 | Laidler | |
| 2018/0236466 A1* | 8/2018 | Laidler | B05B 11/0067 |
| 2018/0297053 A1 | 10/2018 | Buckland | |
| 2019/0053945 A1 | 2/2019 | Hunter | |
| 2019/0074086 A1 | 3/2019 | Ballou, Jr. | |
| 2019/0099071 A1 | 4/2019 | Ehrmann | |
| 2019/0314195 A1 | 10/2019 | Ivri | |
| 2019/0314196 A1 | 10/2019 | Ivri | |
| 2019/0314197 A1 | 10/2019 | Ivri | |
| 2019/0314198 A1 | 10/2019 | Ivri | |
| 2020/0022416 A1* | 1/2020 | Alarcon | A61M 15/0028 |
| 2020/0197218 A1 | 6/2020 | Newell | |
| 2020/0246182 A1 | 8/2020 | Ivri | |
| 2020/0281768 A1 | 9/2020 | Quintana | |
| 2020/0315842 A1 | 10/2020 | Palanker | |
| 2020/0330267 A1* | 10/2020 | Li | A61M 35/00 |
| 2021/0128350 A1 | 5/2021 | Ivri | |
| 2021/0137732 A1 | 5/2021 | Quintana | |
| 2021/0220169 A1 | 7/2021 | Ivri | |
| 2021/0322209 A1 | 10/2021 | Ivri | |
| 2021/0322210 A1 | 10/2021 | Ivri | |
| 2022/0125631 A1 | 4/2022 | Ianchulev | |
| 2022/0160542 A1 | 5/2022 | Palanker | |
| 2022/0192874 A1 | 6/2022 | Ivri | |

FOREIGN PATENT DOCUMENTS

| | | |
|---|---|---|
| CN | 104582647 A | 4/2015 |
| CN | 204813955 U | 12/2015 |
| CN | 107530509 A | 1/2018 |
| EP | 0622035 A1 | 11/1994 |
| EP | 0622035 B1 | 3/1999 |
| EP | 1493410 A2 | 1/2005 |
| JP | 3055480 U | 1/1999 |
| JP | 2007531577 A | 11/2007 |
| JP | 2013535250 A | 9/2013 |
| WO | 1994020875 A3 | 1/1995 |
| WO | 1996000050 A1 | 1/1996 |
| WO | 2001046134 A1 | 6/2001 |
| WO | 2002072169 A2 | 9/2002 |
| WO | 2010078428 A1 | 7/2010 |
| WO | 2012009706 A1 | 1/2012 |
| WO | 2013076682 A1 | 5/2013 |
| WO | 2013090459 A1 | 6/2013 |
| WO | 2013090468 A1 | 6/2013 |
| WO | 2013155201 A2 | 10/2013 |
| WO | 2013158967 A3 | 12/2013 |
| WO | 2016115050 A1 | 7/2016 |
| WO | 2016164830 A1 | 10/2016 |
| WO | 2018136618 A2 | 7/2018 |
| WO | 2018227190 A1 | 12/2018 |
| WO | 2019113483 A1 | 6/2019 |
| WO | 2020010116 A1 | 1/2020 |

OTHER PUBLICATIONS

Ali et al., "Glaucoma and Dry Eye", Ophthalmology, 2009, vol. 116, p. 1232.

Birkhoff et al., "New Devices for Dispensing Ophthalmic Treatments May Be the Key to Managing the Life Cycles of Established Products", 2010, Drug Delivery Technology, vol. 10, pp. 16-21.

Brenton, "CRUK/10/30: TRICON8—Sample collection of ovarian cancer tissues and blood for translational research from patients participating in the CR-UK/MRC ICON8 trial", 2015, online abstract.

Choi et al., "Generation of Controllable Monodispersed Sprays Using Impulse Jet and Charging Techniques", Review of Scientific Instruments, 1990, vol. 61, pp. 1689-1693.

Denion et al., "A 5-Minute Interval between Two Dilating Eye Drops Increases Their Effect", Jul. 19, 2017, Optometry and Vision Science, vol. 94, pp. 838-844.

Electronic Tutorials, "Linear Solenoid Actuator", 2016 [online]; [Retrieved on Oct. 17, 2022], Retrieved from the Internet, <URL: https://www.electronics-tutorials.ws/io/io_6.html>.

Elert, Glenn, "Spherical mirrors", The Physics Hypertextbook, 2021 [online]; [Retrieved on Oct. 17, 2022], Retrieved from the Internet, <URL: https://physics.info/mirrors/>.

Gannon, Megan, "The Best Length for Eyelashes, According to Science", Feb. 24, 2015 [online]; [Retrieved on Oct. 17, 2022], Retrieved from the Internet, <URL: https://www.livescience.com/49934-optimal-length-for-eyelashes-discovered.html>.

Ianchulev et al., "Pharmacodynamic profile of mydriatic agents delivered by ocular piezo-ejection microdosing compared with conventional eyedropper", 2016, Ther. Deliv., vol. 7, pp. 751-760.

Jow et al., "Design and Optimization of Printed Spiral Coils for Efficient Transcutaneous Inductive Power Transmission", IEEE Transactions on Biomedical Circuits and Systems, 2007, vol. 1, pp. 193-202.

Kent, Christopher, "Getting Meds onto the Eye, 21st Century Style", Mar. 15, 2013 [online]; [Retrieved on Aug. 27, 2019], Retrieved from the Internet, <URL: https://www.reviewofophthalmology.com/article/getting-meds-onto-the-eye-21st-century-style>.

Kompella et al., "ISOPT Clinical Hot Topic Panel Discussion on Ocular Drug Delivery", 2019, J. Ocul. Pharmacol. Ther., vol. 35, pp. 457-465.

Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.

Lindblad et al., "Production of Uniform-Sized Liquid Droplets", Journal of Scientific Instruments, 1965, vol. 42, pp. 635-638.

Lux et al., "A Comparative Bioavailability Study of Three Conventional Eye Drops Versus a Single Lyophilisate", Br. J. Ophthalmol., 2003, vol. 87, pp. 436-440.

Macmillan Online Dictionary, "Stream," n.d. [online]; [Retrieved on Dec. 13, 2018]; Retrieved from the Internet, <URL: https://macmillandictionary.com/dictionary/american/stream_1#stream_9>.

Marx et al., "Opthalmic Squeeze Dispenser: Eliminating the Need for Additives in Multidose Preservative-Free Eyecare Formulations", 2017, Drug Development Delivery, vol. 17, pp. 40-44.

Merriam-Webster, "Clamp," 2019 [online]; [Retrieved on Oct. 25, 2022], Retrieved from the Internet, <URL: https://www.merriam-webster.com/dictionary/clamp>.

Merriam-Webster, "Collimate," 2020 [online]; [Retrieved on Oct. 17, 2022], Retrieved from the Internet, <URL: https://www.merriam-webster.com/dictionary/collimated>.

Merriam-Webster, "Stream," n.d. [online]; [Retrieved on Dec. 13, 2018], Retrieved from the Internet, <URL: https://www.merriam-webster.com/dictionary/stream>.

Murube et al., "Classification of Artificial Tears, I: Composition and Properties", Advanced Experimental Medical Biology, 1998, vol. 438, pp. 693-704.

Murube et al., "Classification of Artificial Tears, II: Additives and Commercial Formulas", Advanced Experimental Medical Biology, 1998, vol. 438, pp. 705-715.

Oxford Online Dictionary, "Stream," n.d. [online]; [Retrieved on Dec. 13, 2018]; Retrieved from the Internet, <URL: https://en.oxforddictionaries.com/definition/us/stream>.

Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

Vocabulary.com, "Stream," n.d. [online]; [Retrieved on Dec. 13, 2018]; Retrieved from the Internet, <URL: https://www.dictionary.com/stream>.

* cited by examiner

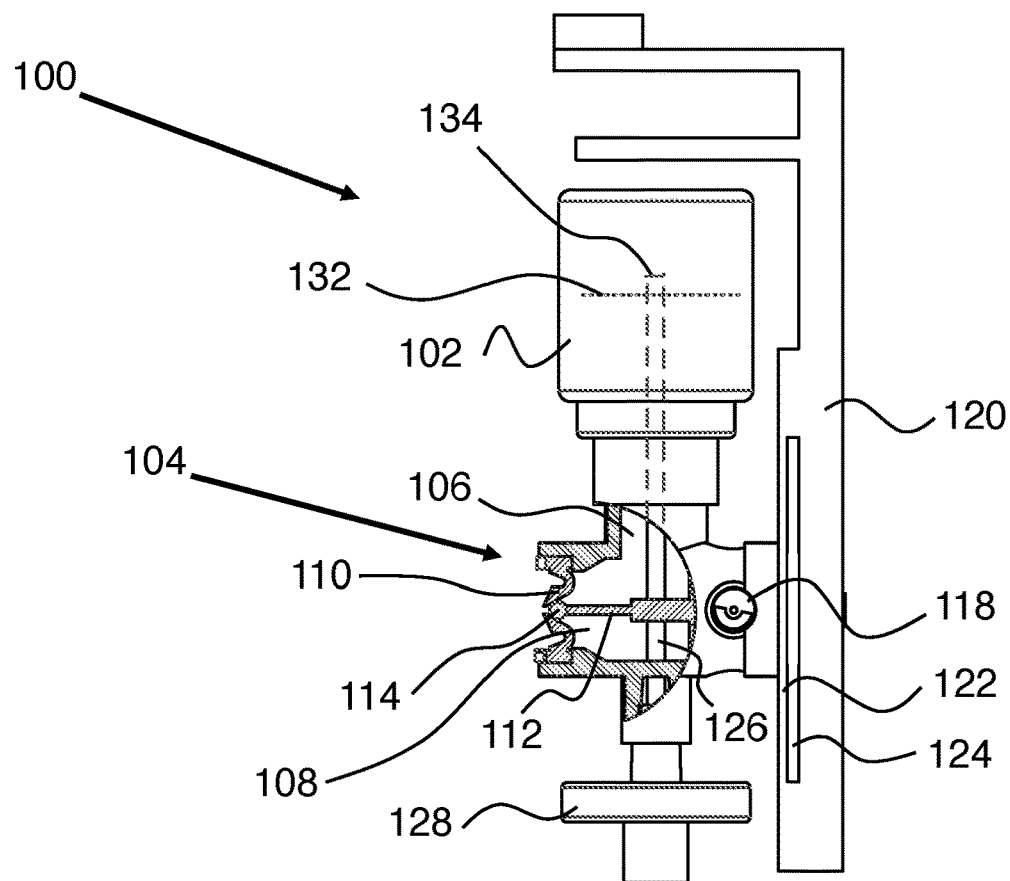
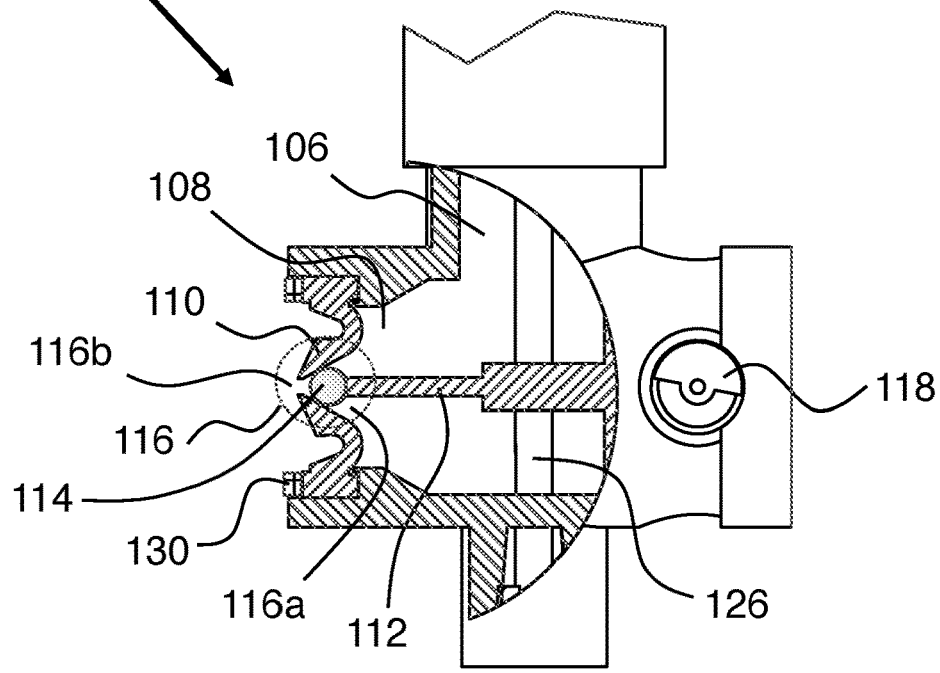
FIG. 1A
FIG. 1B

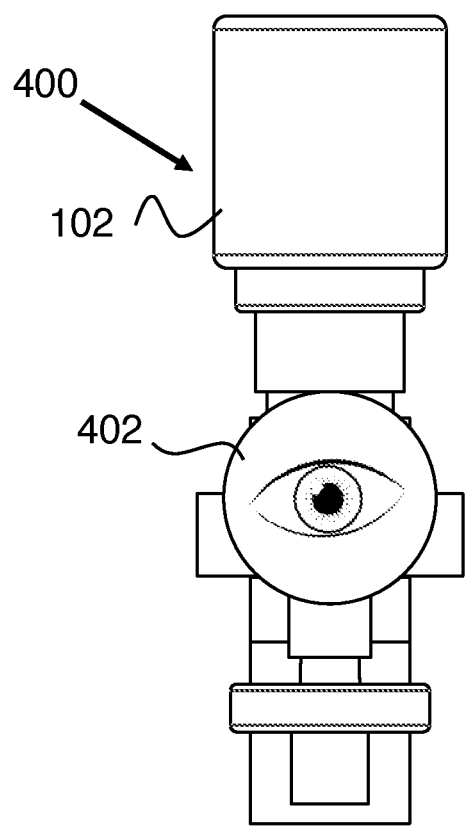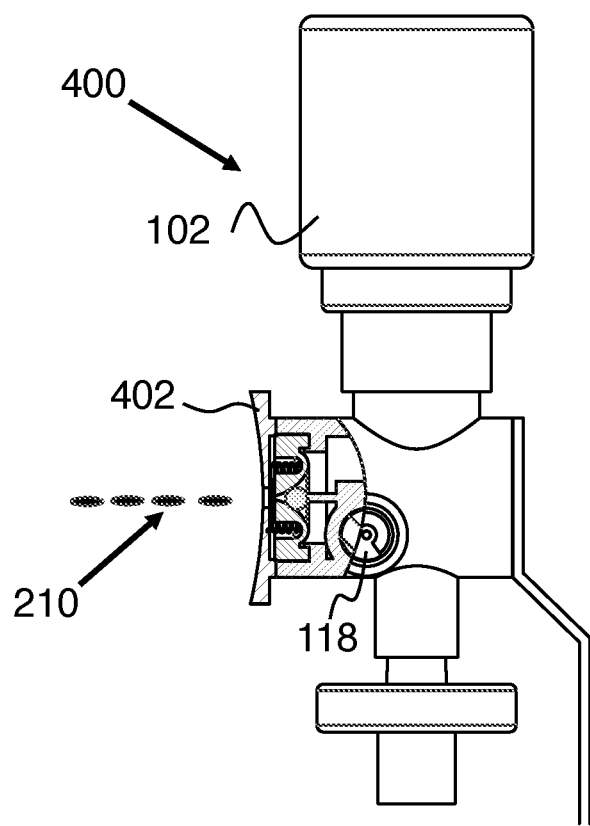
FIG. 4A  FIG. 4B
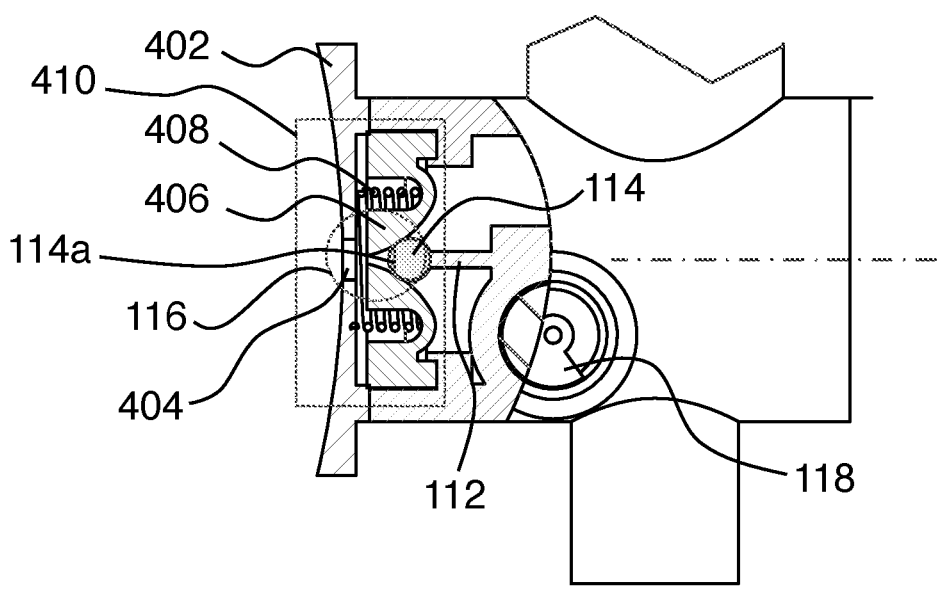
FIG. 4C

HYDRODYNAMICALLY ACTUATED PRESERVATIVE FREE DISPENSING SYSTEM

CROSS REFERENCE TO RELATED APPLICATIONS

This application is a continuation in part of U.S. patent application Ser. No. 17/233,105, filed Apr. 16, 2021, and hereby incorporated by reference in its entirety.

application Ser. No. 17/233,105 claims the benefit of U.S. provisional patent application 63/011,808, filed on Apr. 17, 2020, and hereby incorporated by reference in its entirety.

FIELD OF THE INVENTION

The present invention generally pertains to devices for dispensing fluid medicines and more particularly pertains to such devices that store and deliver ophthalmic preservative-free medicines, specifically configured to increase the ease of use and enhance patient compliance with dosing instructions for the medicine.

BACKGROUND

Ease of dispensing fluid medicines and compliance with dosing instructions are primary concerns with all patients. In particular, preservative-free dispensing bottles such as ophthalmic squeeze dispensers typically require greater actuation force due to a valve mechanism that seals the dispensing nozzle to prevent bacterial ingress and contamination. Such system requires much higher pressure to operate and hence much higher squeeze force is required. In addition, prior art dispensing bottles dispense only in an upside-down orientation which require an inconvenient head maneuver and which together with higher actuation force further increases the inconvenience.

Dispensers of the kind in question are known from the prior art, for example from U.S. Pat. Nos. 6,095,376, 9,676,525, US 2014/0336596, US 2016/0107180, U.S. Pat. Nos. 9,238,532, 8,056,766, 8,863,998, and 10,105,720. The dispenser shown in US 2014/0336596 comprises an outlet channel which connects the liquid reservoir to the outlet opening through an outlet valve which is arranged in the outlet channel and which opens when the bottle is squeezed and pressure is generated. Such preservative-free squeeze bottles typically require about 25-28N of squeeze force (Ophthalmic Squeeze Dispenser—*Drug Development and Delivery* October 2017 Vol. 17 No. 7 page 40). Elderly patients, or other patients lacking enough strength and/or dexterity in their hands, often experience problems dispensing medicine from such bottles.

This work provides preservative free ocular dispensing device that can be held horizontally, or in any convenient orientation while the actuation is done effortlessly by an electrical switch. This provides a cost effective solution that is consistent with standard drug packaging processes.

SUMMARY

Multi-dose preservative-free ocular fluid delivery devices are provided. The fluid delivery device includes a fluid dispensing system and a fluid package for storing a liquid therein and supplying said liquid to the dispensing system. The dispensing system comprises an elongated chamber which includes a check valve which defines a frontal closure to the chamber. The valve is normally closed and hermetically seals the chamber. In this work the chamber includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed.

The check valve can include a flexible plate which includes a conical aperture that extends through its thickness, the valve can further include a stationary spherical member that engages tangentially with the inner wall of the conical aperture to create a hermetic sealed closure. The plate can be made of elastomer that has a modulus of elasticity ranging between 0.1-1.2 GPa. The circumference of the plate can be attached to the chamber by a retaining ring that engages with the chamber in an interference fit to create the hermetically sealed closure.

The conical aperture extends through the thickness of the plate such that droplets are dispensed through the smaller opening of the aperture while the larger side of the aperture is in fluid communication with the chamber.

The spherical member may include an antibacterial coating which covers the area of the spherical member that is between the tangential engagement line and the small opening of the aperture.

The vibrational motor oscillates the chamber and the fluid within the chamber. Consequently, cycles of hydrodynamic pulses are generated causing the valve to cyclically open and dispense fluid. Here this phenomenon is characterized oscillatory interactions between the valve and the surrounding fluid. The hydrodynamic force generated by the momentum of the fluid opens the valve and allows fluid flow through the aperture.

Fluid is dispensed only when the hydrodynamic force is sufficiently high to deform the aperture while otherwise the aperture hermetically seals the chamber. The system prevents ingress of microorganism into the chamber allowing storage of preservative free pharmaceutical. This work provides an electrically operated preservative-free dispensing system that is convenient and cost effective.

BRIEF DESCRIPTION OF THE DRAWINGS

FIG. 1A is a cross sectional view of an embodiment of the invention.

FIG. 1B is a detail cross sectional view of the embodiment of FIG. 1A.

FIG. 4A is a frontal view of an embodiment of the invention.

FIG. 4B is a side view of the embodiment of FIG. 4A.

FIG. 4C is a detail cross sectional view of the embodiment of FIG. 4A.

DETAILED DESCRIPTION

Figure 1C:
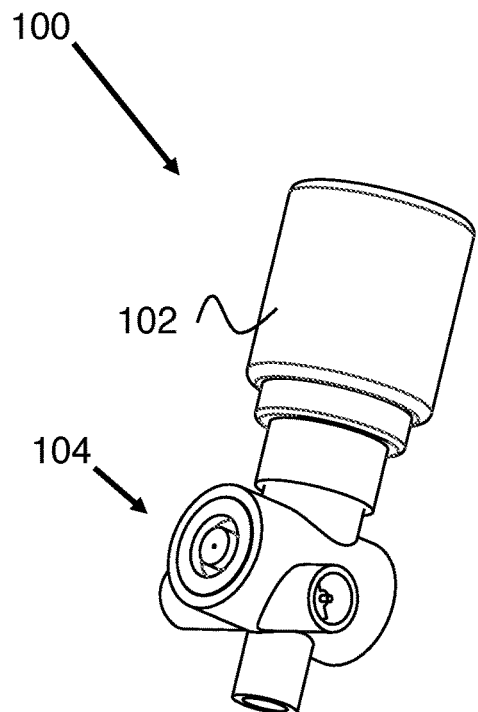
FIG. 1C is a 3D view of the embodiment of FIGS. 1A-B.

This work describes dispensing devices and methods for delivery of preservative-free solutions or suspensions for ocular administration of ophthalmic drugs. The dispensing devices include a droplet ejecting system that is fluidly connected to an ampoule package containing a liquid to be dispensed. The droplet ejecting system includes a chamber having a check valve that defines a front closure to the chamber. The dispensing system further includes a vibration motor that oscillates the chamber and induces hydrodynamic pulses which consequently causes the valve to cyclically open and eject fluid droplets. The valve is normally closed and hermetically sealing the chamber. The valve opens exclusively in response to hydrodynamic pulses induced by the oscillation of the chamber. In this way fluid is dispensed only when the device is actuated while otherwise the aperture hermetically seals the device and prevents ingress of bacterial and microorganisms thereby allowing storage of preservative-free pharmaceutical formulation. The use of a vibration motor further enables convenient and cost effective, electronically controlled administration.

FIG. 1A and FIG. 1B illustrate a side view and an enlarged partial section view, respectively, of a fluid delivery device 100. Delivery device 100 includes a fluid reservoir 102 and dispensing system 104 connected to each other in fluid transmission relationship though passage 106. Dispensing system 104 includes a fluid chamber 108 and also includes a check valve including aperture plate 110 which provides frontal closure to the chamber 108. Referring to FIG. 1B it can be seen that aperture plate 110 includes a conical or tapered aperture 116 (shown inside a dotted circle for clarity) that extends through its center thickness and has a large inlet opening 116a in fluid communication with chamber 108 and a smaller exit opening 116b though which fluid droplets will be dispensed. Aperture plate 110 can be made of a flexible elastomer such as silicone rubber, VersaFlex, manufactured by VersaFlex Incorporated Kansas City, Kansas USA. Other elastomers with Young modulus of elasticity value between 0.5 GPa to 2 GPa can also be used. Dispensing system 104 further includes a stationary spherical member 114 that tangentially engages in pressure transmission relationship with the inlet opening 116a of the conical aperture providing hermetically sealed closure. In a preferred embodiment spherical member 114 is made of high density polyethylene (HDPE) that is harder than silicone thereby creating a tight closure as it engages with the softer aperture plate 110. Spherical member 114 preferably engages in pressure transmission relationship with the conical aperture 116a with a preload force of between 0.01N and 0.05N. The combination of aperture plate 110 and spherical member 114 provides a check valve as described above. Spherical member 114 is supported by pin member 112. Member 114 can have a shape other than spherical, since any shape capable of forming a good seal with aperture plate 110 can be used.

Aperture plate 110 can be retained to dispensing system 104 by a retaining ring 130, thereby creating a hermetically sealed closure.

Dispensing system 100 includes a venting tube 126 that is configured to equalize the pressure inside container 102 as the fluid is dispensed from the device. The opening 134 of venting tube 126 is extended above the fluid level 132 at any orientation that the device is held. Vent tube 126 can be connected via a 0.22 micron filter 128 to assure that the air that enters the device is sterile.

Dispensing system 100 further includes a vibration motor configured to oscillate chamber 108 and the fluid within the chamber. Here this motor is schematically shown as eccentric mechanical load 118 which vibrates the assembly as described when it is rotated by the motor (motor not shown in FIGS. 1A-B, but described below in connection with FIG. 3).

FIG. 1C is a 3D view of the embodiment of FIGS. 1A-B.

Figure 2A:
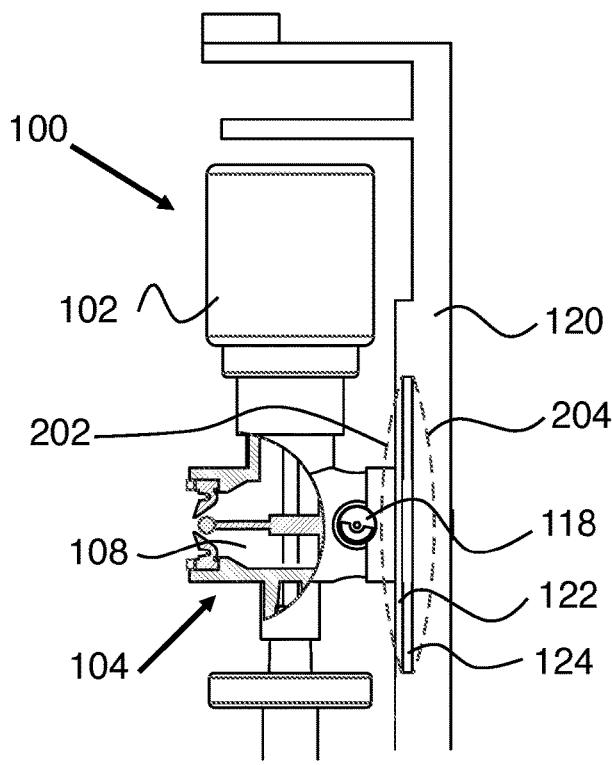
FIG. 2A is a side view and partial cross section view of an embodiment of the invention in operation.
Figure 2B:
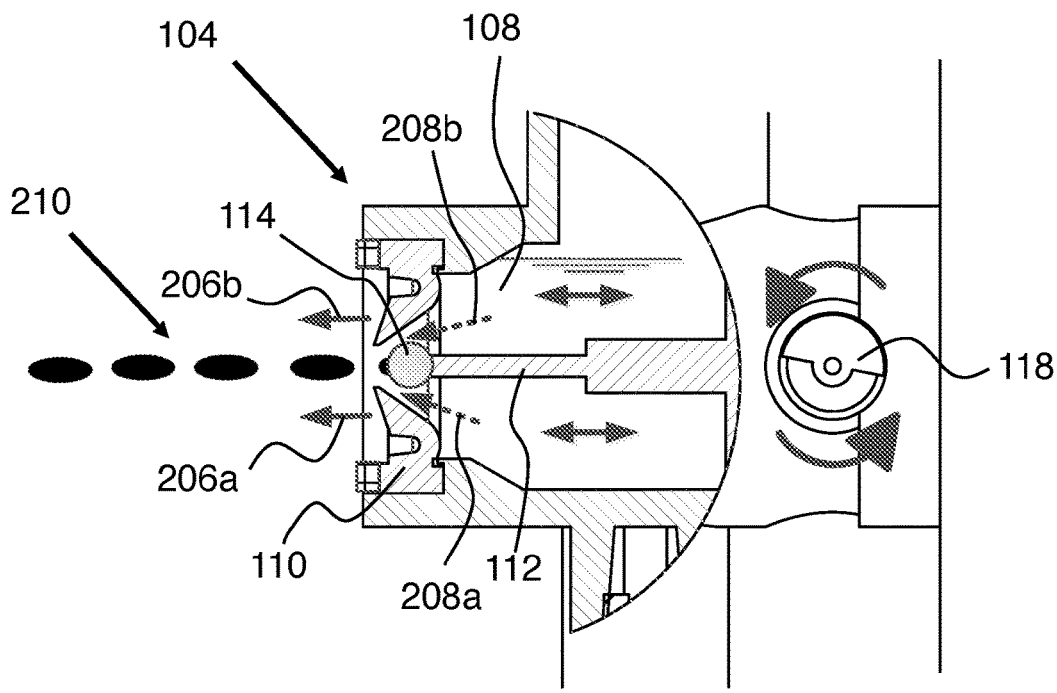
FIG. 2B is a detail cross section view of the example of FIG. 2A.

FIGS. 2A-B illustrate the response of the dispensing system 104 to oscillations. Vibrations of the motor induce oscillation to the body of dispensing system 104 which in turn generates fluid momentum within the chamber due to the dynamical interaction of the fluid with the solid structure of chamber 108. This phenomenon is often referred to as Solid-Fluid-Interaction (SFI). The momentum of the moving fluid exerts force that flexes the aperture plate 110 outwardly in the direction indicated by arrows 206a and 206b causing the aperture plate 110 to disengage from spherical member 114 thereby opening a fluid flow passage as indicated by the arrows 208a and 208b and ejection of fluid droplets 210.

Dispensing device 100 is supported by a flexible beam 122 or other structural embodiments which allows it to oscillate freely, as schematically shown by motion excursions 202 and 204. Preferably the spring constant of the beam 122 is 0.05 N/mm to 0.5 N/mm. For example, beam 122 can be formed by fabricating a slot 124 in support structure 120 such that the resulting beam 122 has a thickness suitable for providing a spring constant as recited above.

Figure 3:
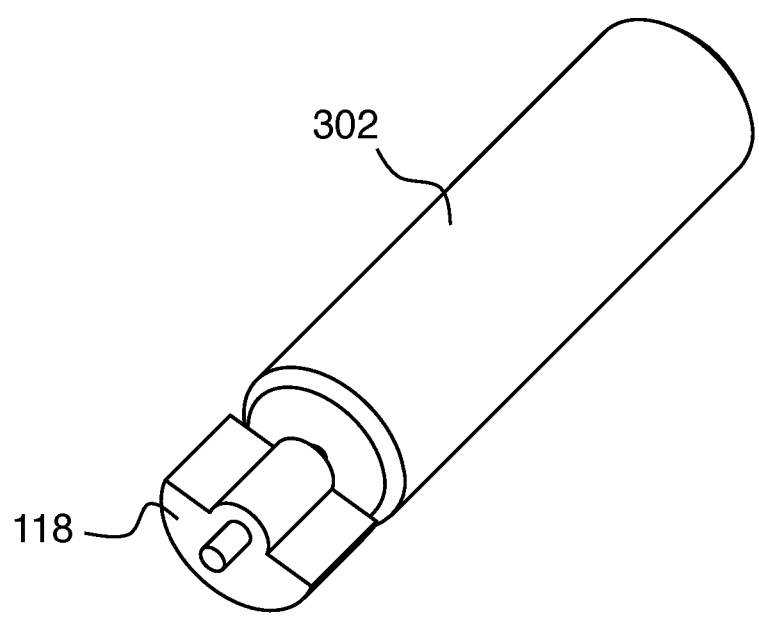
FIG. 3 illustrates a perspective view of a vibration motor as used in embodiments of the invention.

FIG. 3 illustrates an exemplary vibrational motor 302. The DC Motor 302 of this example has a cylindrical body with a diameter of 4 mm and total length of 17 mm. An eccentric flywheel 118 is attached to the motor shaft. The flywheel has a mass of 1.7 grams with a center of mass about 0.7 mm from the center of rotation. The motor receives 4.5-12 VDC and rotates at 6000-12000 RPM generating centrifugal force of 0.3N at a rotation speed of 8000 RPM. Other DC motors that generate centrifugal force of 0.1-1N and rotation speed of 1000-50000 RPM can be used. The motor can be controlled by a timer circuit which is set to provide an ON time as required to deliver a dose of 8-12 micro-liter. The actuation ON time is 60-200 ms depending on the rheology of the fluid in use. A timer circuit which incorporates a 555 timer IC or a microprocessor-based timer with a 12 volt battery such as A23 alkaline battery may be used.

FIGS. 4A-C illustrate an alternative preferred embodiment of dispensing system 400. FIG. 4A illustrates a frontal view and FIG. 4B illustrates a side view of dispensing system 400. Dispensing system 400 includes a concave mirror 402 which assists in aligning device 400 and fluid stream 210 to the eye of the user. In use, dispensing device 400 is positioned in front of the eye such that the image of the eye appears sharply and in the center of mirror to the user. At this point the device is properly positioned in term of the distance of the eye from the nozzle 404 and its angular orientation relative to the eye. Upon actuation, stream 210 will be deposited precisely on the corneal surface of the eye. Device 400 preferably includes a 0.22 micron air filter configured to filter the vented air that flows into device 400, as in the previous example.

Device 400 includes a check valve having an aperture plate 406 with a conical aperture 116 that extends through its thickness. The check valve further includes a spherical member 114 that tangentially engages with the inlet opening of the conical aperture 116. In this example, the check valve also includes a compression spring 408 configured to force aperture plate 406 against spherical member 114. In this way a tight seal is created along the engagement line 114a, thus creating a tight and hermetic closure.

Spherical member 114 can be partially covered with an antimicrobial coating, specifically in the area of spherical member 114 that is not in contact with fluid in the chamber. The coated area thus extends between the engagement line 114a and the outlet of the conical aperture (i.e., to the left of 114a on FIG. 4C)). Examples of antimicrobial coatings include silver in metallic form, silver alloy or a non-metallic material that contains silver including salts of silver chloride and silver sulfadiazine. Other optional material includes biguanide derivatives, chlorohexidine diacetate and chlorohexidine digluconate.

Figure 5A:
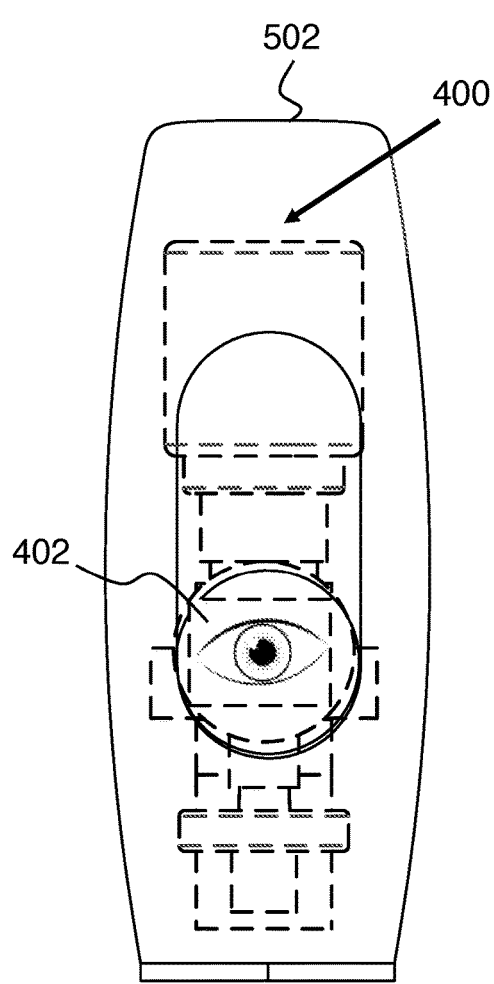
FIG. 5A is a frontal view of an exemplary device enclosed in a housing.
Figure 5B:
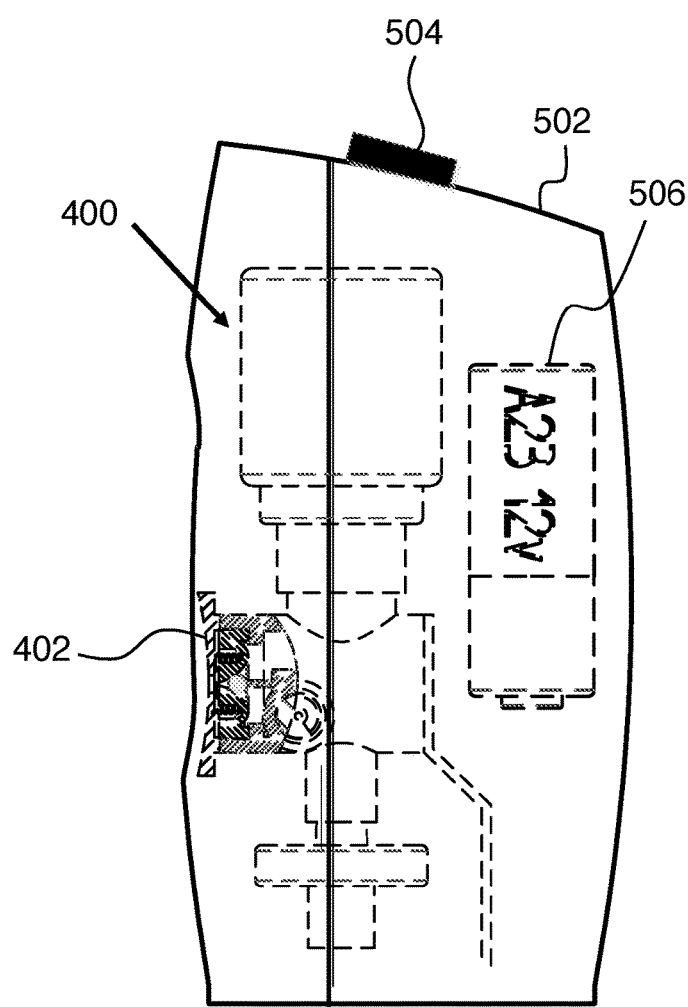
FIG. 5B is a side view of the example of FIG. 5A.

FIGS. 5A-B illustrate frontal and side views, respectively, of a dispensing device 400 packaged in a housing 502. Housing 502 provides a convenient enclosure to the dispensing system 400 that was described in relation in FIGS. 4A-C and is shown with dashed lines here. Housing 502 includes an electrical circuit (not shown) and a 12 volt battery (e.g., type A23) 506. The circuit controls the dispensing period such that a dose of 8-12 microliter is delivered to the ocular surface of the eye. Momentary switch 504 can be used to activate the device 400 such that a stream of droplets is ejected from the aperture as described earlier. FIGS. 5A-B also illustrate the mirror 402 which is visible on the front side of the device. Such a housing can also be used for a dispensing device 100 as described above.

Figures 6A, 6B:
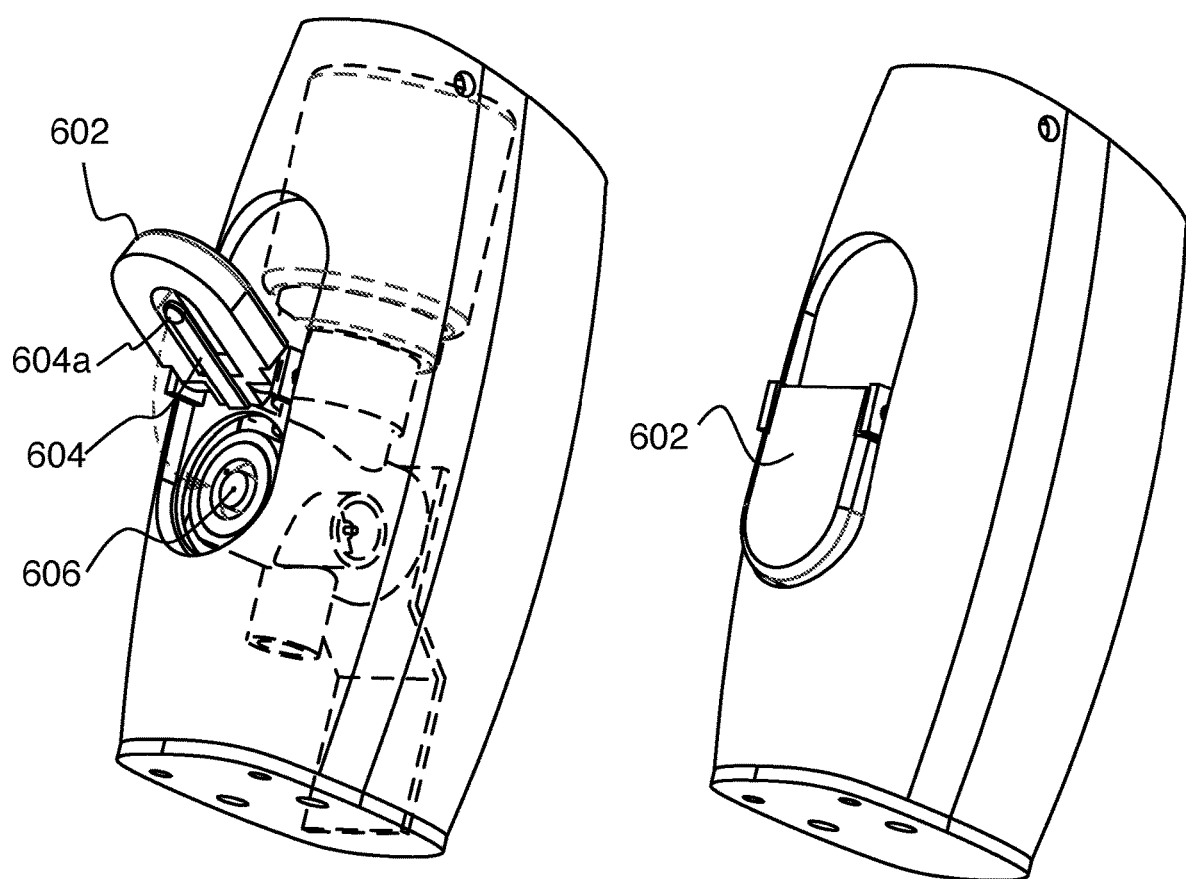
FIGS. 6A-B are perspective views of a device having a housing that includes a swivel cover.

FIGS. 6A-B illustrate some preferred features of housings that can be used with embodiments such as device 100 and device 400 as described above. In this example, the housing includes a swivel cover 602 that covers dispensing nozzle 606 during periods of non-use. Swivel cover 602 provides a means to prevent bacterial contamination on the external areas where a residual fluid may be left following each use. Such residual fluid may contaminate subsequent stream as it is dispensed through the nozzle. Swivel cover 602 preferably includes a flexible member 604 that includes a surface 604a that is covered with antimicrobial coating. Surface 604a engages with the outlet opening of nozzle 606 when the swivel cover 602 is closed as illustrated in FIG. 6B. In this way antipathogen action is achieved.

Alternatively, organic dyes with antiseptic action may also be used. For example, toluidine blue, methylene blue, gentian violet and acridine and related active substances such as acridine orange and acridine yellow as well as ethacridine lactate. Germicidal polymers such as polyhexanide are also possible. Materials that contain additives which contain metal-organic substances with an ionizing effect can also be used. Such additives are available from SteriOne GmbH Berlin, Germany. Examples of antimicrobial coatings that can be used on surface 604a include silver in metallic form, silver alloy or a non-metallic material that contains silver including salt of silver chloride and silver sulfadiazine. Other optional material includes biguanide derivatives, chlorohexidine diacetate and chlorohexidine digluconate.

Closed Loop Motor Control

Optionally, the device includes a drive circuit that controls the rotational speed of the motor. The rotational speed of the motor may be inconsistent due to manufacturing tolerance and other factors. Motor speed inconsistency may cause some devices to emit higher dose and some lower dose depending on the speed of the motor.

To prevent such inconsistency the drive circuit that controls the motor can include an optical sensor that measures the rotational speed of the motor and inputs the value to a microprocessor where the measured speed is compared with the desired target speed. The circuit then increases or decreases the power delivered to the motor until it reaches the target speed. The speed of the motor converges to the desired target speed typically within less than 5 actuations and preferably less than two actuations.

The power delivered to the motor can be controlled by Pulse Width Modulation (PWM). PWM is a method of reducing the average power delivered to an electrical motor or other electrical load by effectively applying short and discrete DC pulses at high frequency, typically in the range of 5-15 KHz.

The voltage or current source can be supplied to the motor by means of a repeating series of "on" and "off" pulses. The on-time is the time during which the DC supply is applied to the motor, and the off-time is the period during which that supply is switched off. The density of the on time relative to the density of the off time controls the power delivered to the motor. The microprocessor increases or decrease the on time until the desired speed is reached.

Figure 7A:
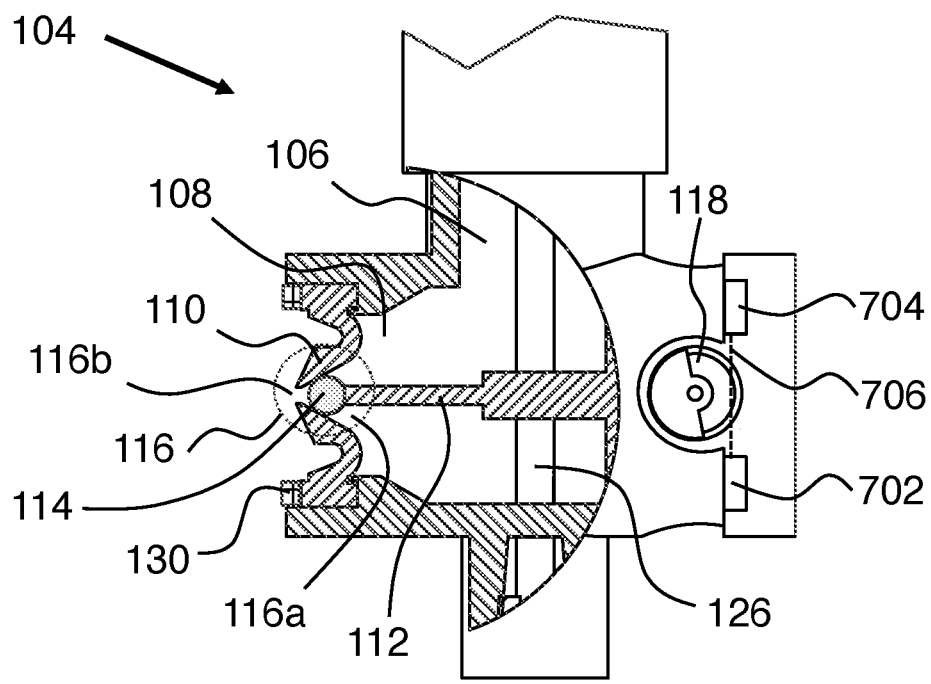
FIGS. 7A-B show operation of an embodiment of the invention including an optical sensor for motor speed.
Figure 7B:
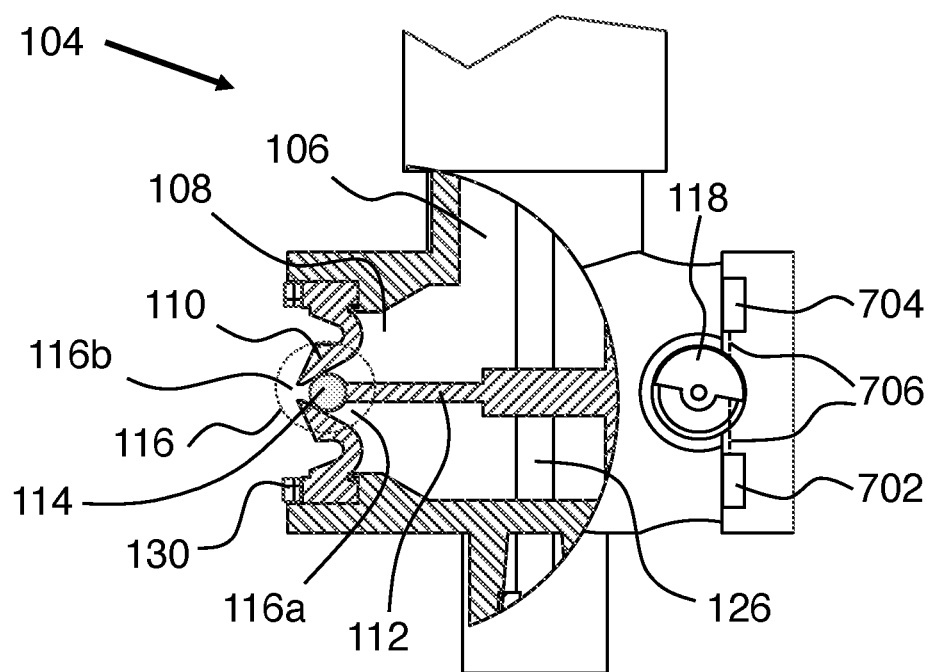

FIGS. 7A-B illustrate the optical sensors that measure the motor speed. The sensors include an LED 702 and a phototransistor 704 positioned coaxially and in predetermined distance from the rotational axis of the motor and its eccentric flywheel 118 such that the flywheel periodically blocks the light. In the first part of the revolution shown in FIG. 7A flywheel 118 is in a rotational position which allow passage of light beam 706 from the LED 702 to reach phototransistor 704 therefore causing the phototransistor to produce an electrical signal. At the second part of the revolution shown in FIG. 7B the light beam 706 from the LED is blocked and interrupted by the flywheel 118. The time between two subsequent interruption signals indicates the cycle time of the motor, the inverse of the cycle time is the number of revolutions per unit time (i.e., the frequency of the motor rotation (which is the same as the frequency of the above-described mechanical excitation)). In this way it is possible to measure the speed of the motor, compare it to the to the target value and make a correction as described earlier.

In this example, an LED is used as the light source and a phototransistor is used as the light detector, but practice of the invention does not depend critically on the choices of optical source and optical detector. Any sources and detectors can be employed.

The invention claimed is:

1. Apparatus for delivering a liquid to an eye of a patient, the apparatus comprising:
    a) a reservoir configured to contain the liquid;
    b) a liquid dispenser in fluid communication with the reservoir, the liquid dispenser having i) a flexible aperture through which the liquid from the reservoir can be dispensed, and ii) a pin member for engagement with the flexible aperture to seal the flexible aperture;
    c) an actuator designed to provide a mechanical excitation to the liquid dispenser that generates a corresponding hydrodynamic excitation of the liquid such that the liquid i) deforms the flexible aperture to disengage the pin member from the flexible aperture; and ii) ejects the liquid through the flexible aperture; and
    d) a sensor positioned to measure frequency of the mechanical excitation and to provide feedback so that movement of the actuator can be adjusted to control its mechanical excitation.

2. The apparatus of claim 1, wherein the actuator includes a vibration motor having an eccentric mechanical load relative to an axis of rotation of the vibration motor.

3. The apparatus of claim 2, wherein the sensor includes an optical source and an optical detector, and wherein an optical path between the optical source and the optical detector is positioned such that rotation of the eccentric mechanical load blocks and unblocks the optical path.

4. The apparatus of claim 2, wherein the liquid dispenser is supported by a flexible member, whereby operation of the vibration motor generates the mechanical excitation to cause hydrodynamic excitation of the liquid by oscillating the liquid dispenser.

5. The apparatus of claim 4, wherein a spring constant of the flexible member is between 0.05 N/mm and 0.5 N/mm.

6. The apparatus of claim 2, further comprising a motor controller configured to control the frequency of the mechanical excitation by automatically adjusting electrical power provided to the vibration motor to cause the frequency of the mechanical excitation to be at a predetermined value.

7. The apparatus of claim 6, wherein electrical power provided to the vibration motor is adjusted using pulse width modulation.

8. The apparatus of claim 1, wherein the aperture is formed in an aperture plate having a Young's modulus of elasticity between 0.5 GPa and 2 GPa.

9. The apparatus of claim 8, wherein a mechanical hardness of the pin member is greater than a mechanical hardness of the aperture plate.

10. The apparatus of claim 1, wherein the aperture is tapered to be narrower at an outlet of the aperture than at an inlet of the aperture.

11. The apparatus of claim 1, wherein the pin member is stationary relative to the liquid dispenser.

12. The apparatus of claim 1, wherein a tip of the pin member engages with the aperture, and wherein the tip of the pin member has a spherical shape.

13. The apparatus of claim 12, wherein the tip of the pin member is partially or completely coated with an antibacterial coating.

14. The apparatus of claim 13, wherein the antibacterial coating covers at least a part of the tip of the pin member that is outside the liquid dispenser in a normally closed configuration.

15. The apparatus of claim 1, wherein a preload force engaging the pin member with the aperture in a normally closed configuration is between 0.01 N and 0.05 N.

16. The apparatus of claim 1, wherein the reservoir includes a vent.

17. The apparatus of claim 16, wherein the vent includes a filter configured to ensure that air that enters the reservoir is sterile.

18. The apparatus of claim 1, further comprising a concave mirror configured to provide an in-focus image of the eye to the patient when the apparatus is positioned properly to deliver the liquid to the eye of the patient.

* * * * *